United States Patent
Knopeck et al.

(10) Patent No.: US 9,308,199 B2
(45) Date of Patent: *Apr. 12, 2016

(54) MEDICAMENT FORMULATIONS

(75) Inventors: Gary Knopeck, Lakeview, NY (US);
Jeremy Diringer, Morristown, NJ (US);
Louis Herena, Scarsdale, NY (US);
Rajiv R. Singh, Getzville, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 1470 days.

This patent is subject to a terminal disclaimer.

(21) Appl. No.: 11/375,826

(22) Filed: Mar. 15, 2006

(65) Prior Publication Data

US 2006/0269484 A1 Nov. 30, 2006

Related U.S. Application Data

(60) Continuation-in-part of application No. 10/837,525, filed on Apr. 29, 2004, now Pat. No. 7,279,451, and a division of application No. 10/837,526, filed on Apr. 29, 2004, now Pat. No. 7,524,805, and a division of application No. 10/837,521, filed on Apr. 29, 2004, now Pat. No. 7,655,610.

(60) Provisional application No. 60/662,579, filed on Mar. 16, 2005.

(51) Int. Cl.
| | |
|---|---|
| A61K 48/00 | (2006.01) |
| A61K 38/17 | (2006.01) |
| A61K 31/44 | (2006.01) |
| A61L 9/04 | (2006.01) |
| A61K 38/28 | (2006.01) |
| A61K 31/56 | (2006.01) |
| C09K 3/30 | (2006.01) |

(52) U.S. Cl.
CPC .............. *A61K 31/44* (2013.01); *A61K 31/56* (2013.01); *A61K 38/28* (2013.01); *C09K 3/30* (2013.01)

(58) Field of Classification Search
None
See application file for complete search history.

(56) References Cited

U.S. PATENT DOCUMENTS

| | | | |
|---|---|---|---|
| 2,889,379 A | 6/1959 | Ruh et al. | |
| 2,931,840 A | 4/1960 | Marquis | |
| 2,996,555 A | 8/1961 | Rausch et al. | |
| 3,472,826 A | 10/1969 | Potts et al. | |
| 3,659,023 A | 4/1972 | Regan | |
| 3,723,318 A * | 3/1973 | Butler | 252/67 |
| 3,884,826 A | 5/1975 | Phares, Jr. et al. | |
| 4,086,407 A | 4/1978 | Fozzard | |
| 4,465,786 A | 8/1984 | Zimmer et al. | |
| 4,798,818 A | 1/1989 | Baizer et al. | |
| 4,900,874 A | 2/1990 | Ihara et al. | |
| 5,162,594 A | 11/1992 | Krespan | |
| 5,290,539 A * | 3/1994 | Marecki | 222/402.2 |
| 5,532,419 A | 7/1996 | Van Der Puy et al. | |
| 5,545,777 A | 8/1996 | Morikawa et al. | |
| 5,574,192 A | 11/1996 | Van Der Puy et al. | |
| 5,679,875 A | 10/1997 | Aoyama et al. | |
| 5,710,382 A | 1/1998 | Dunmead et al. | |
| 5,776,434 A * | 7/1998 | Purewal et al. | 424/45 |
| 5,900,185 A | 5/1999 | Tapscott | |
| 5,969,198 A | 10/1999 | Thenappan et al. | |
| 5,986,151 A | 11/1999 | Van Der Puy | |
| 6,023,004 A | 2/2000 | Thenappan et al. | |
| 6,031,141 A | 2/2000 | Malikarjuna et al. | |
| 6,063,970 A * | 5/2000 | Boyce et al. | 570/168 |
| 6,066,769 A | 5/2000 | Nappa et al. | |
| 6,111,150 A * | 8/2000 | Sakyu et al. | 570/167 |
| 6,300,378 B1 * | 10/2001 | Tapscott | 514/743 |
| 6,369,284 B1 | 4/2002 | Nappa et al. | |
| 6,423,298 B2 | 7/2002 | McNamara | |
| 6,548,719 B1 | 4/2003 | Nair et al. | |
| 6,638,495 B2 | 10/2003 | Weers et al. | |
| 6,809,226 B1 | 10/2004 | Pennetreau et al. | |
| 6,958,424 B1 | 10/2005 | Nair et al. | |
| 6,977,316 B1 | 12/2005 | Mukhopadhyay et al. | |
| 7,026,520 B1 | 4/2006 | Mukhopadhyay et al. | |
| 7,026,521 B1 | 4/2006 | Mukhopadhyay et al. | |
| 7,071,367 B1 | 7/2006 | Mukhopadhyay et al. | |
| 7,132,578 B1 | 11/2006 | Mukhopadhyay et al. | |
| 7,135,601 B2 | 11/2006 | Mukhopadhyay et al. | |
| 7,189,884 B2 | 3/2007 | Mukhopadhyay et al. | |
| 7,196,236 B2 | 3/2007 | Mukhopadhyay et al. | |
| 7,524,805 B2 * | 4/2009 | Singh et al. | 510/408 |

(Continued)

FOREIGN PATENT DOCUMENTS

| | | |
|---|---|---|
| EP | 0522639 | 1/1993 |
| EP | 0644173 | 3/1995 |

(Continued)

OTHER PUBLICATIONS

"Honeywell HFO-1234ze Blowing Agent", http://www51.honeywell.com/sm/lgwp-fr/common/documents/FP_LGWP_FR_Honeywell-HFO-1234ze_Literature_document.pdf, accessed Oct. 5, 2013.*
Banks et al. "Preparation of 2,3,3,3-tetrafluoropropene from trifluoroacetylacetone and sulphur tetrafluoride", Journal of Fluorine Chemistry, 82, 1997, pp. 171-174.*
Banks, et al., Journal of Fluorine Chemistry, vol. 82, Issue 2, pp. 171-174 (1997).
Database Beilstein, Beilstein Institute for Organic Chemistry, M. Van Der Puy: J. Fluorine Chemistry, vol. 81, No. 2, 1997, pp. 187-192 XP002424669.
Database Beilstein, Beilstein Institute for Organic Chemistry, Haszeldine, Steele: J. Chem. Soc. 1953, p. 1592, 1597, XP0022424670.
Database WPI Week 199812, AN 1998-126110, XP002427152, Derwent Publications Ltd., London, GB & JP 10 007605A (Central Glass Co Ltd) Jan. 13, 1998 abstract.
Database Beilstein, XP002426121.

(Continued)

Primary Examiner — Bethany Barham
Assistant Examiner — Melissa Javier
(74) Attorney, Agent, or Firm — Colleen D. Szuch

(57) ABSTRACT

Medicinal compositions, and devices, methods and systems which use the compositions, comprising a propellant and at least one medicinally active compound. The propellant comprises at least one fluoroolefin having at least two but less than seven carbon atoms.

25 Claims, 1 Drawing Sheet

(56) References Cited

U.S. PATENT DOCUMENTS

| | | |
|---|---|---|
| 2003/0060670 A1 | 3/2003 | Nair et al. |
| 2003/0114537 A1* | 6/2003 | Gavin et al. ............. 514/650 |
| 2004/0119047 A1* | 6/2004 | Singh et al. ............. 252/71 |
| 2004/0127383 A1* | 7/2004 | Pham et al. ............. 510/412 |
| 2004/0136920 A1 | 7/2004 | Akehurst et al. |
| 2004/0256594 A1* | 12/2004 | Singh et al. ............. 252/71 |
| 2005/0020862 A1 | 1/2005 | Tung et al. |
| 2005/0080302 A1 | 4/2005 | Baker et al. |
| 2005/0090698 A1 | 4/2005 | Merkel et al. |
| 2005/0171391 A1 | 8/2005 | Janssens et al. |
| 2005/0233934 A1* | 10/2005 | Singh et al. ............. 510/412 |
| 2007/0112227 A1 | 5/2007 | Mukhopadhyay et al. |
| 2007/0112228 A1 | 5/2007 | Mukhopadhyay et al. |
| 2007/0112229 A1 | 5/2007 | Mukhopadhyay et al. |
| 2007/0112230 A1 | 5/2007 | Mukhopadhyay et al. |
| 2007/0129580 A1 | 6/2007 | Mukhopadhyay et al. |

FOREIGN PATENT DOCUMENTS

| | | |
|---|---|---|
| EP | 0974571 * | 7/1999 |
| EP | 0974571 * | 1/2000 |
| EP | 974571 A2 | 1/2000 |
| GB | 844597 | 8/1960 |
| JP | 11140002 | 5/1999 |
| JP | 2000169404 | 6/2000 |
| JP | 2000178543 | 6/2000 |
| JP | 2003535017 A | 11/2003 |
| WO | 9008752 | 8/1990 |
| WO | 9504021 | 2/1995 |
| WO | 96/01797 A | 1/1996 |
| WO | 98/42645 | 3/1998 |
| WO | 98/21171 | 5/1998 |
| WO | 98/33754 A | 8/1998 |
| WO | 98/52542 A | 11/1998 |
| WO | 99/48993 | 9/1999 |
| WO | WO00/00215 * | 1/2000 |
| WO | 00/35458 A | 6/2000 |
| WO | 00/39242 | 7/2000 |
| WO | 01/07384 | 2/2001 |
| WO | 03027051 | 4/2003 |
| WO | 2004/037752 A2 | 5/2004 |
| WO | 2004037913 A2 | 5/2004 |
| WO | 2005/012212 | 2/2005 |
| WO | 2005/042451 A | 5/2005 |
| WO | 2005108332 | 11/2005 |
| WO | 2005108334 | 11/2005 |
| WO | 2007019355 A | 2/2007 |

OTHER PUBLICATIONS

Dickson, R.S., Fluorcarbon-Aluminium Compounds, Aust. J. Chem., 1972, 25, 761-8.

Gambareto et al., "The Reaction of chlorine monofloride with unsaturated compounds", 1976, XP00246119.

Haszeldine R.N., Free-radical Additions to Unsaturated Systems. Part XVII. Reaction of Trifluoroiodomethane with Mixtures of Ethylene and Vinyl Fluoride and of Ethylene and Propene, Journal of Chemical Society, Section C: (3), 414-21. p. 415.

Henne, Albert L., et al., Chlorinated Derivatives of 2-Floropropane J. American Chemical Society, Jul. 11, 1941: pp. 2692-2694, vol. 63.

J Burdon et al.: J. Fluorine Chemistry, vol. 40, pp. 283-318, XP002424668.

Knunyants, I. L. et al. Reaction of Fluoro Olefins, Institute of Heteroorganic Compounds, Bulletin of the Academy of Sciences of USSR, Division of Chemical Sciences—ISSN 0568-5230, p. 1312-1317.

Kunshenko B V et al.: Reaction of Organic Compounds with SF4-HF-Hallogenating System VII, 1992, XP002344564.

March, J. Advanced Organic Chemistry, 1997, pp. 631-636, McGraw-Hill International Book Company, XP002427150.

Vittorio Minanari, A Novel Systensis of Perhalogenated Alkenes, J. Org. Chem. 1992, 57, 5018-5019.

Montzka et al., "Scientific Assessment of Ozone Depletion: 2002," World Meteorological Organization Global Ozone Research and Monitoring Project—Report No. 47, pp. 1.28-1.35.

* cited by examiner

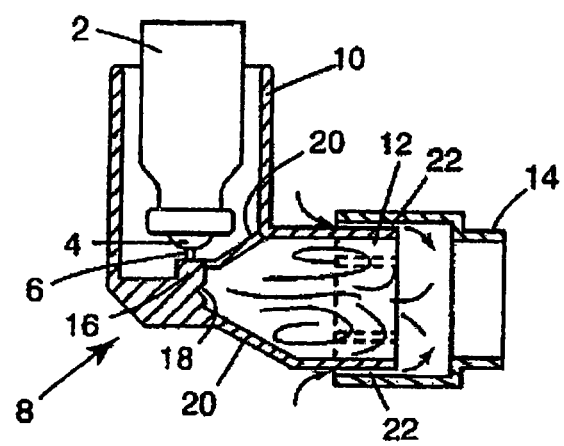

MEDICAMENT FORMULATIONS

RELATED APPLICATIONS

The present application is related to and claims the priority benefit of the following U.S. Applications. The present application claims priority to U.S. Provisional Patent Application Ser. No. 60/662,579, filed Mar. 16, 2005. The present application is also a divisional of U.S. patent application Ser. No. 10/837,521 filed Apr. 29, 2004 (now U.S. Pat. No. 7,655,610, issued Feb. 2, 2010), entitled "Heat Transfer Fluid Comprising Trans-1,3,3,3-tetrafluoropropene," and a divisional of U.S. patent application Ser. No. 10/837,526 filed Apr. 29, 2004 (now U.S. Pat. No. 7,524,805, issued Apr. 28, 2009), entitled "Azeotrope-like Compositions of Tetrafluoropropene and Carbon Dioxide, the contents each of which are incorporated by reference herein. The present application is also a continuation-in-part of U.S. patent application Ser. No. 10/837,525, filed Apr. 29, 2004 (now U.S. Pat. No. 7,279,451).

FIELD OF THE INVENTION

This invention relates to medicament delivery compositions, systems, devices and methods. In particular aspects, this invention relates to medicinal aerosol formulations, methods and devices, such as those used in connection with pulmonary, nasal, buccal or topical administration of medicaments.

BACKGROUND OF THE INVENTION

Metered dose inhalers (MDIs) have long been used to deliver medicaments, such as bronchodilator drugs and steroids, to the areas of patients needing treatment. Compared with oral administration of bronchodilators, inhalation therapy using MDIs frequently has the advantage of relatively rapid onset of action and relatively low instance of systemic side effects.

In general, MDIs are dependent upon the propulsive force of a propellant to help transport the medicament to the area or areas needing treatment, which sometimes are referred to herein as the "target area." The propellant has heretofore generally comprised a mixture of liquefied chlorofluorocarbons (CFC's) selected to have the vapor pressure necessary to produce the desired propulsive force while at the same time providing stability of the medicament formulation. Methane and ethane series CFCs, such tetrachloromethane (CFC-11), trichlorofluoromethane (CFC-12) and 1,2 dichlorotetrafluoroethane (CFC-114), have commonly been used as propellants in aerosol formulations for inhalation administration.

The use of CFCs has environmental drawbacks. It is now known that CFC's tend to react with the ozone layer around the earth and thereby result in some level of ozone depletion. As a result various governmental and international organizations have been engaged in efforts to reduce or eliminate the use of CFCs. The volume of CFCs which have been used in connection with MDIs may be considered low compared to other uses, such as refrigerants and blowing agents. Nevertheless, a potential ozone depletion advantage may be achieved by reducing or eliminating CFCs from MDIs and other medicament delivery systems.

Because of the potential damage to the earth's ozone layer caused by chlorine-containing compounds (such as chlorofluorocarbons (CFCs), hydrochlorofluorocarbons (HCFCs) and the like), there has thus been an increasing need for new fluorocarbon and hydrofluorocarbon compounds and compositions that offer alternatives with reduced ozone depletion potential. For example, efforts are under way to replace chlorine-containing propellants with non-chlorine-containing compounds that will not deplete the ozone layer, such as hydrofluorocarbons (HFCs).

U.S. Pat. No. 5,776,434—Purewal, et al. has recognized the ozone depletion problem of CFCs and has proposed the use of a non-chlorine containing compound, namely, 1,1,1,2-tetrafluoroethane (sometimes referred to herein as HFA-134a or HFC-134a) as a propellant for medicinal aerosol formulations when used in combination with a surface active agent and an adjuvant having a higher polarity than 1,1,1,2-tetrafluoroethane. However, in 1998 the International Programme on Chemical Safety (IPCS), published a Concise International Chemical Assessment Document (No. 11) indicating that 1,1,1,2-tetrafluorethane has a significant global warming potential.

HFC-227ea (1,1,1,2,3,3,3-heptafluoropropane) has also been proposed as low ozone depletion potential substitute for CFCs in MDIs. However, this compound also has a significant global warming potential.

U.S. Pat. No. 6,111,150 describes chlorofluor- and fluoro-substituted propenes as being "useful as an intermediate of medicines..." (col.2, l. 4). However, there is no disclosure or suggestion of MDIs or any of the propellant materials used in MDIs. U.S. Pat. Nos. 3,723,318 and 3,884,826 each describes the use of trifluoropropene in connection with aerosol propellants and refrigerants, but there is no disclosure or suggestion in these patents relating to MDIs, nor is there any disclosure or suggestion regarding the use of tetrafluoropropene as an aerosol or in connection with MDIs.

Bromine-containing halocarbon additives have been suggested for use in connection with efforts to reduce the flammability of numerous materials, including aerosol propellants, in U.S. Pat. No. 5,900,185—Tapscott. The additives described in this patent are said to be characterized by high efficiency and short atmospheric lifetimes, that is, low ozone depletion potential (ODP) and a low global warming potential (GWP). The patent discloses the use of such compounds in amounts of from about 0.1 to about 20 percent by weight.

While the brominated olefins described in Topscott may have some level of effectiveness in connection with use as anti-flammability agents in connection with certain materials, there is no disclosure of the use of such materials as an aerosol or propellant. Furthermore, it is believed that such compounds may also have certain disadvantages. For example, applicants have come to recognize that many of the compounds identified in Topscott will have a relatively low efficiency as a blowing agent due to the relatively high molecular weight of such compounds. In addition, it is believed that many of the compounds disclosed in Tapscott will encounter problems when used as a blowing agent due to the relatively high boiling point of such compounds. Moreover, it is understood by applicants that many compounds which have a high level of no means substitution may possess undesirable toxicity properties and/or other undesirable properties, such as potentially environmentally undesirable bioaccumulation.

Thus, applicants have recognized a need for compounds, compositions, systems, devices and methods for medicament delivery that at once provide relatively low ozone depletion potential and relatively low global warming potential. Moreover, applicants have recognized that any composition, including any propellant contained therein, must also possess properties which ensure the efficacy of the medicament, such as medicament stability, low- or no-toxicity, and compatibility with the other components of the medicament delivery system.

SUMMARY

Applicants have found that many of the shortcomings of the prior compositions can be overcome and/or that many of the above-noted needs can be satisfied by medicinal compositions, and by devices, methods and systems which use same, comprising a propellant and at least one medicinally active compound, said propellant comprising at least one fluoroolefin, preferably hydrofluoroolefin, which is a medicinally acceptable carrier for said medicinally active compound and having at least two but less than seven, preferably less than six, and even more preferably less than five carbon atoms. As used herein, the term medicinally acceptable carrier refers to materials which are at least not substantially harmful to the intended recipient of the medicinally active compound. As used herein, the term fluoroolefin means an organic compound comprising at least carbon and fluorine and at least one carbon-carbon double bond, with other substituents being optionally present. As used herein, the term hydrofluoroolefin means an organic compound comprising carbon, hydrogen and fluorine and at least one carbon-carbon double bond, with other substituents being optionally present, although in certain preferred embodiments chlorine is not present. As used herein, the terms "medicinal," "medicament," and the like are used in their ordinary broad sense to refer to any and all materials or substances which have, or at least are believed to have, the property of healing, treating or relieving disease, injury or other ailment, and/or the pain or other symptoms of same, and/or of diagnosing same, such would include for example drugs and biologically active substances. Thus, the term "medicinally active compound," is used herein to refer to a compound or combinations of compounds which are effective, or at least are believed to be effective, in a medicinal sense.

In certain preferred embodiments, the fluoroolefin of the present invention comprises, preferably comprises in major proportion, and even more preferably consists essentially of, one or more compounds of Formula I as follows:

$$XCF_zR_{3-z} \quad (I)$$

where X is a $C_2$ or a $C_3$ unsaturated, substituted or unsubstituted, alkyl radical, each R is independently F, Br, I, Cl or H, and z is 1 to 3, but where it is generally not preferred for R to be Cl. In preferred embodiments, the Formula I compound is tetrafluoropropene, more preferably 1,1,1,3-tetrafluoropropene (HFO-1234ze) and/or 1,1,1,2-tetrafluoropropene (HFO-1234yf). The term HFO-1234ze is used herein generically to refer to 1,1,1,3-tetrafluoropropene, independent of whether it is the cis- or trans-form. The terms "cisHFO-1234ze" and "transHFO-1234ze" are used herein to describe the cis- and trans-forms of 1,1,1,3-tetrafluoropropene respectively. The term "HFO-1234ze" therefore includes within its scope cisHFO-1234ze, transHFO-1234ze, and all combinations and mixtures of these. In certain preferred embodiments, the composition comprises, the trans-isomer of 1,1,1,3-tetrafluoropropene.

In certain of the preferred composition of the present invention the propellant does not have a substantial negative effect on atmospheric chemistry. More specifically, in the preferred compositions the propellant of the present invention has a very low or negligible contribution to ozone depletion in comparison to some of the heretofore commonly used halogenated species. The preferred compositions thus have the advantage of not contributing substantially to ozone depletion. The preferred compositions also do not contribute substantially to global warming compared to many of the hydrofluoroalkanes which have been commonly used.

BRIEF DESCRIPTION OF THE DRAWING

The invention will now be described with reference to the accompanying drawings in which:

FIG. 1 represents a cross-section through an inhaler in accordance with one embodiment of the invention.

DETAILED DESCRIPTION OF PREFERRED EMBODIMENTS

I. The Compositions

It is contemplated that the compositions of the present invention can be used in a wide variety of forms, and all such forms are within the broad scope of the present invention. In general, it is preferred that present compositions are in a form suitable for delivery to the particular site on or in the human or other mammal needing treatment, or to a site which is the preferred location for introduction into the body, even if the treatment or diagnosis is required at other areas. For example, the preferred compositions of the present invention are generally well adapted for delivery through the mouth, nose, ears and/or other mucosal membranes, or by transdermal application. It is possible, therefore, that the compositions of the present invention may be delivered to the lungs for treatment of a malady occurring in the lungs or as a mechanism for introducing the medicament into the system (e.g., bloodstream) of the user in order to treat a malady elsewhere.

The amount of medicinal compound(s) present relative to the amount of propellant can vary widely in accordance with the present invention, and all such proportions are believed to be adaptable for use within the scope hereof, provided of course that the total amount of medicinally active agent is therapeutically effective, or at least believed to be therapeutically effective by the doctor or other professional prescribing the medicament. In certain preferred embodiments, however, the present compositions comprise at least about 50% by weight, and even more preferably from about 60% to about 99%, or more, by weight, of propellant based upon the total weight of the composition. Furthermore, it is preferred in certain embodiments that the composition comprise from about 0.01% to about 0.5% by weight of medicinally active compounds, although it is appreciated that lesser or greater amounts may be used depending upon the particular medicament, the prescribed dosage and other numerous factors.

A. The Medicinally Active Compound

Although it is contemplated that the medicinally active compounds of the invention may be present in a wide variety of forms, it is preferred in many embodiments that the medicinally active agent or compound is part of a solution, dispersion, suspension, emulsion, or the like. As explained in more detail hereinafter, the medicinal compounds of the present invention are frequently present as particles having various sizes and other physical properties, although fine particulate form is generally preferred for the formation of stable, substantially uniform dispersions, suspensions, etc. of the medicinal compounds. It will be appreciated, in addition, that in certain embodiments two or more medicinally active substances are included in the present compositions, and in yet further embodiments, at least one of said medicinally active substances is present in a dissolved form in a liquid phase and/or at least one other of said medicinally active substances is present in suspended form in a fluid, preferably a liquid phase.

In certain embodiments, the medicinal compounds of the present invention are preferably used in micronized or microparticulate form. Such forms preferably exhibit a relatively hollow and porous morphology, and also preferably have a mass average aerodynamic diameter (MAAD) of not greater than about 10 microns, but preferably less than about 5 microns. Medicinal compounds of this type are preferred for use in many MDI applications. The use of such micro-particulate medicinal compounds in combination with the propellant components of the present invention is believed to produce especially stable and effective compositions.

One problem associated with many medicinal compositions, particularly those adapted for use in connection with MDIs, is the tendency of the individual particles of the medicinally active compound to agglomerate. As described in detail hereinafter, certain embodiments of the present invention include one or more adjuvants to stabilize the composition against this and other types of undesirable change. In addition, certain embodiments hereof enhance the stability of the composition by using and/or altering particle morphology to reduce attractive forces between the dispersed components and to reduce density differences, thereby retarding degradation of the suspensions, dispersions, etc. by flocculation, sedimentation or creaming. Such enhancements in certain embodiments may facilitate uniform dose delivery by MDIs, and allow for more concentrated dispersions. In such preferred embodiments, at least a substantial proportion of the medicinally active particles, and preferably a major proportion, have hollow and/or porous perforated microstructures that substantially reduce attractive forces, such as van der Waals forces. Without being bound by or to any particular theory of operation, the use of perforated (or porous) microstructures or microparticulates that are permeated or filled by the surrounding fluid or suspension medium (which generally includes the propellant of the present invention), is believed to significantly reduce disruptive attractive forces between the particles. Moreover, the components of the dispersions may be selected to minimize differences in polarizabilities (i.e. reduced Hamaker constant differentials) and further stabilize the preparation. In certain preferred embodiments, the dispersions of the present invention are substantially homogeneous with only minor differences in density between particles, preferably as defined by the perforated microparticulates and the suspension medium. Such perforated microparticles are disclosed in U.S. Pat. No. 6,638,495, which is incorporated herein by reference.

With respect to the particular type of medicinal compound or agent, those skilled in the art will appreciate that any therapeutic or diagnostic agent may be incorporated into the present composition, preferably the dispersions of the present invention. For example, the medicinal compound may be selected from the group consisting of antiallergics, bronchodilators, bronchoconstrictors, pulmonary lung surfactants, analgesics, antibiotics, leukotriene inhibitors or antagonists, anticholinergics, mast cell inhibitors, antihistamines, antiinflammatories, antineoplastics, anesthetics, anti-tuberculars, imaging agents, cardiovascular agents, enzymes, steroids, corticosteroids, short acting beta-agonists, long-acting beta-agonists, genetic material, viral vectors, antisense agents, proteins, peptides, anti-asthma medication and combinations of any two or more thereof. Particularly preferred medicinal agents for use in accordance with the invention include anti-allergics, peptides and proteins, bronchodilators and anti-inflammatory steroids for use in the treatment of respiratory disorders, such as asthma and chronic obstructive pulmonary disorder (COPD), by inhalation therapy.

Exemplary medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, mometasone furoate, tripedane, cortisone, prednisone, prednisilone, dexamethasone, betamethasone, or triamcinolone acetonide; antitussives, e.g. noscapine; bronchodilators, e.g. ephedrine, epinephrine, adrenaline, fenoterol, formoterol, isoprenaline, metaproterenol, salbutamol (albuterol), salmeterol xinafoate, terbutaline; diuretics, e.g. amiloride; anticholinergics, e.g. ipratropium bromide, tiotropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, LHRH, nafarelin, goserelin, leuprolide, interferon, rhu IL-1 receptor, macrophage activation factors such as lymphokines and muramyl dipeptides, opioid peptides and neuropeptides such as enkaphalins, endorphins, renin inhibitors, cholecystokinins, DNAse, growth hormones, leukotriene inhibitors and the like. In addition, bioactive agents that comprise an RNA or DNA sequence, particularly those useful for gene therapy, genetic vaccination, genetic tolerization, or antisense applications, may be incorporated in the disclosed dispersions as described herein. Representative DNA plasmids include pCMV.beta. (available from Genzyme Corp, Framington, Mass.) and pCMV-.beta.-gal (a CMV promotor linked to the *E. coli* Lac-Z gene, which codes for the enzyme .beta.-galactosidase), and any combination of two or more of these. In many prefer embodiments, at least two different medicinally active compounds in combination, are included in the composition.

B. The Propellant

In preferred embodiments, one of the primary functions of the propellant of the present invention is to provide a source of kinetic energy to aid in delivery of the medicinal compounds to the desired site. MDIs, for example, generally depend upon the propulsive force of the propellant system used in its manufacture. The propellant system preferably not only provides the desired vapor pressure to, but it also at least does not degrade, and preferably enhances the stability of the suspension. It is contemplated that the present propellant systems may be used to deliver solubilized or suspended agents and/or, in preferred embodiments, to deliver selected medicinal compound in fine particulate form to provide a dispersion. Thus, in certain preferred embodiments of the present invention the propellant also serves to carry and/or solubilize and/or suspend one or more of the medicinal compounds of the present invention.

With respect to the preferred compound(s) for use in the present invention, the propellant comprises, preferably consists essentially of, and in some preferred embodiments consists of, at least one fluoroolefin, preferably a hydrofluorolefin containing from 3 to 4 carbon atoms, preferably three carbon atoms. The hydrofluoroolefin compounds of the present invention are sometimes referred to herein for the purpose of convenience as "HFOs" if they contain at least one hydrogen, at least one fluorine and no chlorine. Although it is contemplated that certain HFOs of the present invention may contain two carbon-carbon double bonds, such compounds at the present time are not considered to be preferred.

As mentioned above, the present compositions preferably comprise one or more compounds in accordance with Formula I. In preferred embodiments, the compositions include compounds of Formula II below:

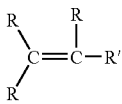

(II)

where each R is independently F, Br, I, Cl or H, but preferably not Cl

R' is $(CR_2)_nY$,

Y is $CRF_2$ and n is 0 or 1.

In highly preferred embodiments, Y is $CF_3$, n is 0 and at least one of the remaining Rs is F.

Applicants believe that, in general, the compounds of the above identified Formulas I and II are generally effective as propellants in medicinal compounds as described herein, particularly in connection with aerosol compositions. However, applicants have surprisingly and unexpectedly found that certain forms of the compounds having a structure in accordance with the formulas described above exhibit a highly desirable low level of toxicity compared to other of such compounds. As can be readily appreciated, this discovery is of potentially enormous and critical importance to the formulation of medicinal compositions, since pharmacologically and medicinally acceptable excipients should generally not have a substantially level of toxicity. More particularly, applicants believe that relatively low toxicity levels are associated with compounds of Formula II, preferably wherein Y is $CF_3$, wherein at least one R on the unsaturated terminal carbon is H, and at least one of the remaining Rs is F. Applicants believe also that all structural, geometric and stereoisomers of such compounds are effective and of beneficially low toxicity.

In highly preferred embodiments, especially embodiments comprising the low toxicity compounds described above, n is zero. In certain highly preferred embodiments the compositions of the present invention comprise, and in certain embodiments consists essentially of, one or more tetrafluoropropenes. As mentioned above, the term "HFO-1234" is used herein to refer to all tetrafluoropropenes. Among the tetrafluoropropenes, HFO-1234yf is particularly preferred in many embodiments. HFO-1234ze, in the cis- and/or trans-forms are may be preferred also in certain embodiments. As also mentioned above, the term HFO-1234ze is used herein generically to refer to 1,1,1,3-tetrafluoropropene, independent of whether it is the cis- or trans-form, and the terms "cisHFO-1234ze" and "transHFO-1234ze" are used herein to describe the cis- and trans-forms of 1,1,1,3-tetrafluoropropene respectively. In certain preferred embodiments, the HFO-1234ze comprises a combination of transHFO-1234ze and cisHFO-1234ze, and more preferably from about 90% to about 99% trans on the basis of total HFO-1234ze, with the cis isomer comprising from about 1% to about 10% of the same basis. The propellant compositions of the present invention therefore comprise in certain embodiments a combination of cisHFO-1234ze and transHFO1234ze, preferably in a cis:trans weight ratio of from about 1:99 to about 10:99, more preferably from about 1:99 to about 5:95, and even more preferably from about 1:99 to about 3:97.

Although the properties of cisHFO-1234ze and transHFO-1234ze differ in at least some respects, it is contemplated that each of these compounds is adaptable for use, either alone or together with other compounds including its stereoisomer, in connection with each of the applications, methods, systems and devices described herein. For example, while transHFO-1234ze may be preferred for use in certain systems because of its relatively low boiling point (−19° C.), it is nevertheless contemplated that cisHFO-1234ze, with a boiling point of +9° C., also has utility in connection with the present invention. Accordingly, it is to be understood that the terms "HFO-1234ze" and 1,1,1,3-tetrafluoropropene refer to both stereo isomers, and the use of this term is intended to indicate that each of the cis- and trans-forms applies and/or is useful for the stated purpose unless otherwise indicated.

HFO-1234 compounds are known materials and are listed in Chemical Abstracts databases. The production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786, each of which is incorporated herein by reference. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$. In addition, methods for producing compounds in accordance with the present invention are described generally in connection with pending U.S. patent application entitled "Process for Producing Fluoropropenes" bearing (U.S. Appln. No. 13/226,019, now Pat. No. 8,247,624), which is also incorporated herein by reference.

The present compositions, particularly those comprising HFO-1234 (including HFO-1234yf and HFO-1234ze), are believed to possess properties that are advantageous for a number of important reasons. For example, applicants believe, based at least in part on mathematical modeling, that the fluoroolefins of the present invention will not have a substantial negative affect on atmospheric chemistry, being negligible contributors to ozone depletion in comparison to some other halogenated species. The preferred compositions of the present invention thus have the advantage of not contributing substantially to ozone depletion. The preferred compositions also do not contribute substantially to global warming compared to many of the halogenated molecules presently in use.

In certain preferred forms, compositions of the present invention have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100-year time horizon, as defined in "The Scientific Assessment of Ozone Depletion, 2002, a report of the World Meteorological Association's Global Ozone Research and Monitoring Project," which is incorporated herein by reference.

In certain preferred forms, the present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the fluoroolefins, particularly the Formula I compounds, and even more particularly HFO-1234, contained in the propellant component of present compositions can vary widely, depending upon numerous factors relevant to each particular use of the composition, and propellants comprising more than trace amounts and up to and including 100% of the compound are within the broad scope of the present invention. Moreover, the compositions of the present invention can be azeotropic, azeotrope-like or non-azeotropic. In preferred embodiments, the present compositions comprise HFO-1234, preferably HFO-1234ze, in amounts from about 5% by weight to about 99% by weight, and even more preferably from about 5% to about 95%.

Many compounds that are not fluorolefins, and particularly not in accordance with Formula (I), may be combined with the such compound(s) of the present invention to form the propellant, and the presence of all such compounds is within the broad scope of the invention. In certain preferred embodiments, the present compositions include, in addition to the fluroolefin compound(s), preferably of Formula (I) and even more preferably HFO-1234ze, one or more other hydrofluoralkenes, as well as hydrofluoroalkanes, fluorocarbons, perfluorocarbons, fluorocarbon/hydrocarbon diblocks, hydrocarbons, alcohols and ethers.

In certain preferred embodiments, the propellant of the present invention comprises one or more compound(s) of Formula (I), preferably in an amount of about 1 percent by weight to about 99 percent by weight based on the weight of the total propellant, and one or more hydrofluorocarbons (HFCs), such as, for example hydrofluoroethanes (eg., pentafluoroethane (HFC-125), 1,1,2,2-tetrafluoroethane (HFC-134) and 1,1,1,2-tetrafluoroethane (HFC-134a)); and hydrofluorpropanes (eg., 1,1,1,2,3,3,3-heptafluoropropane (HFC-227ea)). The relative amount of the compound(s) of the present invention, particularly the compounds of formula (I), and the above noted additional propellant components, as well as any additional components (described hereinafter) which may be included in present compositions, can vary widely within the broad scope of the present invention according to the particular application for the composition.

C. Other Components

As is known to those skilled in the art, many modifiers, additives and adjuvants, as well as other propellants, may be included in medicinal compositions, and all such components are believed to be readily adaptable for use with the compositions of the present invention. For example, medicinal preparations are frequently prepared in the form of powdered preparations, sometimes referred to as micronized powders. However, such powders frequently tend to aggregate due to hydrophobic or electrostatic interactions between the fine particles. Such cohesion may be at least partially overcome by incorporating into the present compositions one or more anti-aggregating agents. One type of anti-aggregating agent believed to be adaptable for use with the present compositions are larger carrier particles, for example, lactose which is thought to inhibit aggregation.

In addition, the present compositions may include one or more other special purpose adjuvants, such as a cosolvent(s) and/or surfactant(s) that enhance the composition. Many embodiments of the present compositions may not need co-solvent(s) and/or surfactant(s), depending upon the interaction between the medically active compound and the propellant. In certain embodiments a cosolvent may be necessary or desirable to help dissolve or suspend the medicinally active compound in the propellant. One important characteristic of the cosolvent which is preferred or required for many embodiments is that the cosolvent be pharmacologically tolerable. In certain of such embodiments, therefore, the cosolvent(s) are selected from the group consisting of pharmacologically tolerable hydrocarbons, pharmacologically tolerable alcohols, pharmacologically tolerable esters, pharmacologically tolerable ethers, water and combinations of any two or more thereof. From among such hydrocarbons, it is preferred in certain embodiments that the compositions comprise one or more of propane, butane, isobutene, n-pentane, isopentane, neopentane. From among such alcohols, it is preferred in certain embodiments that the compositions comprise one or more of ethyl alcohol, isopropyl alcohol, propylene glycol, and glycerol. From among such esters, isopropyl mysristate may be mentioned, and from among such ethers, dimethyl ether may be mentioned. Any two or more of any of these may be used in combination. Of course, it is generally preferred in most embodiments that the cosolvent or combinations of cosolvents be miscible, and even more preferably fully miscible, with the propellant.

Although the amount of cosolvent used in the present compositions may vary widely, depending upon numerous factors including the particular type of medicament and propellant being used, in many embodiments it is preferred that the composition have a propellant:cosolvent weight ratio of from about 50:50 to about 99:1.

For certain embodiments in which the present medicinal composition is in the form of a suspension, and particularly an aerosol suspension, the composition includes also surfactant(s), in addition to, but preferably rather than, a cosolvent. While not intending to be bound by or to any particular theory of operation, it is believed in such embodiments that the surfactant would help to prevent agglomeration of the particles, the adhesion to of the particles to the walls of the container, and provide for lubrication of the dispensing valve. In such embodiments, it is generally preferred that the surfactant, when present, is in the composition in the amount of not greater than about 5% by weight of the composition, although those skilled in the art will appreciate that greater amounts may be included depending upon the particulars of each composition and its intended application. While it is contemplated that certain surfactants or combinations of surfactants may not be fully soluble in the present medicinal compositions, or in the propellant in particular, it is generally preferred to use surfactants which are soluble in the propellant, and preferably substantially fully soluble in the propellant under conditions of storage and/or use. Although the amount of surfactant used in the present compositions may vary widely, depending upon numerous factors including the particular type of medicament and propellant being used, in many embodiments is preferred that the compositions have a surfactant:medicament weight ratio of from about 1:100 to about 10:1.

Exemplary surfactants which may be used, alone or combination with one another in accordance with the present invention include C5-C20 fatty alcohols, C5-C20 fatty acids, C5-C20 fatty acid esters, lecithin, glycerides, propyleneglycol esters, polyoxyethanes, polysorbates, sorbitan esters and carbohydrates. More specific examples of acceptable surface active agents include oleic acid, sorbitan mono-, di- or tri-oleate, and combinations of two or more thereof.

Many embodiments of the present invention, particularly those in which the composition is in the form of a suspension, emulsion or dispersion, and particularly an aerosol thereof, preferably include a stabilizing agent. Stabilizing agents for such suspensions, emulsions and dispersions are well known, and it is contemplated that all such stabilizing agents are adaptable for use in accordance with the present invention. Exemplary stabilizing agents include, either alone or in combination, hydrochloric acid, sulphuric acid, nitric acid, phosphoric acid, ascorbic acid, citric acid, benzalkonium chloride, ethylene diamine tetraacetic, and pharmacologically tolerable salts thereof. Although it is contemplated that the stabilizing agents of the present mentioned it may be included in the compositions in widely varying amounts, it is generally preferred in many embodiments that the stabilizing agent is present in an amount of from about 40 to about 100 ppm by weight of the composition.

As mentioned above, many medicinal compositions provide medicinal compounds in micro-particulate form, which preferably exhibits a relatively hollow and porous morphology. Such forms are within the scope of the present invention and are commonly used in MDIs. The use of such micro-particulate medicinal compounds in combination with the propellant components in accordance with the present invention is believed to produce especially stable compositions.

The compositions of the present invention, particularly compositions comprising or consisting essentially of HFO-1234, are capable of providing nonflammable, liquefied gas propellant and aerosols that do not contribute substantially to global warming or ozone depletion. The present compositions therefore provide in certain preferred embodiments substantially nonflammable, liquefied gas propellants having very low Global Warming and Ozone Depletion Potentials.

Although the present compositions may be prepared in many forms, in certain embodiments the composition is in the form of an aerosol product for medical use. The aerosol in preferred embodiments contains at least one propellant of the present invention along with one or more active medicinal ingredients, and optionally inert ingredients, stabilizers, surfactant, other propellants and/or solvents. The propellant of the present invention preferably at least contributes to, and even more preferably provides substantially all of the force that expels the product in aerosolized form. In accordance with preferred embodiments of the present invention, the propellant is a liquefied gas under conditions of storage and use.

II. Devices and Methods

One aspect of the present invention provides a device for the delivery, preferably by inhalation, of a medicament composition of the present invention. In certain preferred embodiments, the device comprises a container, preferably an aerosol canister, containing a pressurized medicament or formulation of the present invention and preferably having a metered dose dispensing valve operable between non-dispensing and dispensing positions. The present devices preferably also comprise an actuator, which in preferred embodiments comprises a housing adapted to receive the aerosol container and to define a chamber in fluid communication with a patient port for introducing the medicament into the oral and/or nasal cavity of the patient, preferably in the form of a mouthpiece and/or nasal adapter. The actuator also preferably includes a nozzle block adapted to receive the valve stem of the dispensing valve, the nozzle block preferably comprising a passage in fluid communication with the valve stem and terminating in an orifice for directing medicament from the valve stem into the chamber.

By way of example but not by way of limitation, in certain embodiments the invention device is constructed such that airflow due to patient inhalation is prevented or reduced in the vicinity of the orifice at all times or only during dispensing of the medicament from the valve. Either of such arrangements has the effect of substantially reducing the velocity of the emitted spray compared to an inhaler which allows free flow of air in the vicinity of the nozzle block during dispensing of the medicament.

In certain embodiments, the actuator is constructed such that the distance from the nozzle to the mouthpiece is from approximately 1 to 15 cm, preferably 4 to 6 cm, with a chamber/mouthpiece diameter from 1 to 4 cm, 0.5 to 1 cm in the case of a nasal adapter.

In certain preferred but non-limiting embodiments, the actuator possess air inlets which enable the patient to inhale though the patient port, preferably without encountering significant resistance since the patient may have breathing difficulties when taking the medication, for example, during an asthma attack. However, the air inlets, for example in the mouthpiece, preferably do not concentrate the airflow into an area that is too narrow, as this will give a high velocity of incoming air which will deflect the spray onto the wall of the mouthpiece opposite the air inlets. In certain preferred embodiments the air inlets are positioned downstream of the nozzle, in the region of the turbulent zone and/or downstream of the turbulent zone. The positioning and direction of the air inlets may also affect the deposition of medicament within the chamber and mouthpiece. In one arrangement air inlets comprise a series of holes and optionally may be interdispersed with fluid deflection structures on the wall of the chamber, to direct air into the turbulent zone to mix air with the aerosol stream. Further, the mouthpiece may be constructed of porous material to allow a multiplicity of finely divided air vents to provide air flow over a larger surface area.

In certain embodiments the actuator possesses air inlets upstream of or in the vicinity of the nozzle but the air inlets are blocked when the valve is fired to release the aerosol spray. The air inlets are opened after the spray has been released by which time the velocity of the stream will have been reduced and the turbulent zone formed. Upon inhalation, an airflow is established from the air inlets to the mouthpiece which entrains the residual aerosol spray. The actuator may include additional air inlets downstream of the nozzle, as described above with respect to the first embodiment. These downstream air inlets do not need to close during release of the aerosol spray.

In certain embodiments, a porous membrane is present to introduce air into or downstream of the turbulent zone. One advantage of the use of such a membrane is that the air is introduced more uniformly and diffusely around the circumference of the spray, thereby acting as a buffer between the turbulent flow and the wall. The effect is to reduce drug deposition in the device. The membrane may optionally be protected from dirt or contact by the user's lips by an additional part of the mouthpiece. When present, it is preferred that the porous membrane material (50) must not significantly impede the patient's ability to inhale through the device. A suitable material is Whatmann No. 4 filter paper; but other materials may be used, such as those used in cylindrical air filters or membrane filters, or such as those formed by sintering polymers. A preferred porous membrane material is in the form of a cylinder made by fusing together small pellets of polypropylene.

For certain medicaments, it is preferred to configure the device so as to reduce contact between the medicament and parts of the patient's body that it is not intended to contact. For example, residues of the medicament deposited on internal surfaces of actuators may be fingered and transferred to other body parts. In such cases, the device may be configured to include one or more fluid flow deflectors to allow the spray to pass through, whilst limiting access by the patient to internal surfaces of the actuator. Of course, the device may be configured for intranasal delivery. This is normally quite undesirable, since the medicaments were designed for delivery to the respiratory system and may not have an appropriate effect when deposited in the oropharynx and allowed to enter the digestive tract. In an effort to overcome this problem, certain embodiments of the present device include the provision of a holding volume, commonly called a spacer, in which the medicament is fired. The spacer preferably allows the velocity of the medicament to be reduced and may also allow some propellant evaporation to occur. Spacers can improve the performance of a metered dose inhaler by reducing oropharyngeal deposition.

One preferred embodiment is disclosed in connection with FIG. 1 This device comprises an aerosol canister (2) equipped with a metered dose dispensing valve (4) having a valve stem (6). The actuator, generally shown at (8), comprises a housing (10) which receives the aerosol container (2), a chamber (12) and a mouthpiece (14). A nozzle block (16) receives the valve stem (6) and has a passage (not shown) terminating in an orifice (18) which directs spray from the aerosol valve into the chamber. The housing comprises solid walls (20) in the vicinity of the nozzle block so that there can be no air flow through the device in the vicinity of the orifice. Air inlet passages (22) are positioned towards the end of the chamber (12) and are directed towards the mouthpiece (14).

In operation, the aerosol valve is fired and a metered dose of aerosol formulation exits the orifice (18) into the chamber (12). Preferably there is no air flow in the vicinity of the orifice (18), in which case the spray is rapidly decelerated and a turbulent zone is formed within the chamber (12). As the patient breathes through the mouthpiece (14) air passes through the inlets (22) towards the mouthpiece (14) forming a sheath of air around the spray of aerosol formulation. In such preferred embodiments as disclosed in FIG. 1, the inhaler provides substantially reduced deposition in the oropharynx of the patient compared with a standard press-and-breathe inhaler, which is also within the scope of the present devices.

In other embodiments the mouthpiece may have a bulbed configuration to provide an increase in cross-sectional area of the mouthpiece downstream of the turbulent zone followed by a decrease in cross-sectional area at the extreme downstream end of the mouthpiece. In such embodiments, the bulbed configuration acts in a similar manner to a conventional spacer.

Certain aspects of the present invention thus provide inhalers, and preferably metered dose inhalers (MDIs) for the treatment of asthma and other chronic obstructive pulmonary diseases and for delivery of medicaments to accessible mucous membranes or intranasally. The present invention thus includes methods for treating ailments, diseases and similar health related problems of an organism (such as a human or animal) comprising applying a composition of the present invention containing a medicament or other therapeutic component to the organism in need of treatment. In certain preferred embodiments, the step of applying the present composition comprises providing an MDI containing the composition of the present invention (for example, introducing the composition into the MDI and then discharging the present composition from the MDI.

Although the present invention has been described and exemplified above in connection with certain preferred embodiments, it is not necessarily limited to these examples and embodiments. The scope of the invention is defined in accordance with the claims presented hereinbelow and/or presented hereinafter.

What is claimed is:

1. A medicinal composition comprising: (a) a medicinally acceptable a propellant; and (b) at least one medicinally active compound, said propellant having a toxicity level that is not substantially harmful to the intended recipient of said medicinal compound and comprising at least 50% by weight of HFO-1234, wherein said HFO-1234 consists essentially of transHFO-1234ze and wherein said at least one medicinally active compound is in the form of a suspension, dispersion, emulsion or a solution with said propellant.

2. The medicinal composition according to claim 1 wherein said HFO-1234 consists of transHFO-1234ze.

3. The medicinal composition according to claim 1 wherein the propellant consists essentially of transHFO-1234ze.

4. The medicinal composition according to claim 1 wherein said propellant further comprises one or more other propellants selected from the group consisting of other hydrofluoralkenes, hydrofluoroalkanes, fluorocarbons, perfluorocarbons, fluorocarbon/hydrocarbon diblocks, hydrocarbons, alcohols, ethers and combinations of two or more thereof.

5. The medicinal composition according to claim 4 wherein said other propellants are selected from the group consisting of pentafluoroethane (HFC-125); 1,1,2,2-tetrafluoroethane (HFC-134); 1,1,1,2-tetrafluoroethane (HFC-134a); 1,1,1,2,3,3,3-heptafluoropropane (HFC-227ea); and combinations thereof.

6. The medicinal composition of claim 1 wherein said propellant has a Global Warming Potential (GWP) of not greater than about 1000.

7. The medicinal composition of claim 1 wherein said propellant has a Global Warming Potential (GWP) of not greater than about 100.

8. The medicinal composition of claim 1 wherein said propellant has an Ozone Depleting Potential (ODP) of not greater than about 0.05.

9. The medicinal composition of claim 1 in the form of a medicinal preparation for propellant driven application wherein said at least one medicinally active compound is in the form of a suspension or a solution with said propellant.

10. The medicinal composition of claim 9 wherein at least one other active substance is in the form of particles suspended or in solution in the liquid phase.

11. The medicinal composition according to claim 9 wherein said medicinally active compound comprises a combination of two or more medicinally active substances solubilized in said propellant.

12. The medicinal composition according to claim 1 wherein said medically active compound is selected from the group consisting of corticosteroids, anti-inflammatories, anti-allergics, long-acting beta agonists, short-acting beta agonists, anticholinergics, proteins and peptides, anti-infectives, pain management, vaccines, hormones, gene therapy vectors, oligonucleotides, immunoglobulins and anti-IgE monoclonal antibodies.

13. The medicinal composition according to claim 1 wherein said medically active compound comprises one or more medically active ingredients selected from the group consisting of Salbutamol (albuterol), chiral albuterol, budesonide, epinephrine, formoterol, salmeterol xinafoate, beclomethasone dipropionate, budesonide, cromoglycinic acid, fenoterol, flunisolide, fluticasone propionate, mometasone furoate, insulin, nedocromil, orciprenaline, oxitropium bromide, repreterol, disodium cromoglycate, pirbuterol, isoprenaline, adrenaline, rimiterol, terbutalin, tiotropium, ipratropium bromide, epinephrine, omalizumab, the esters, salts, solvates or combinations thereof.

14. The medicinal composition of claim 1 further comprising at least one surfactant selected from the group consisting of C5-C20 fatty alcohols, C5-C20 fatty acids, C5-C20 fatty acid esters, lecithin, glycerides, propyleneglycol esters, polyoxyethanes, polysorbates, sorbitan esters and carbohydrates, or combinations thereof.

15. The medicinal composition of claim 1 further comprising a cosolvent.

16. The medicinal composition of claim 15 wherein said cosolvent has a greater polarity than said propellant.

17. The medicinal composition of claim 16 wherein said cosolvent comprises one or more alcohols.

18. The medicinal composition of claim 17 wherein said alcohol is selected from the group consisting of ethanol, isopropanol, propylene glycol, glycerol, and combinations thereof.

19. An inhaler for medicinal composition comprising a canister containing a medicament formulation, a chamber capable of fluid communication with said canister, and a patient port for introducing said medicinal composition from said chamber to the oral or nasal cavity of the intended user, said medicinal composition comprising: (a) medicinally acceptable propellant; and (b) at least one medicinally active compound, said propellant having a toxicity level that is not substantially harmful to the intended recipient of said medicinal compound and comprising at least 50% by weight of HFO-1234, wherein said HFO-1234 consists essentially of transHFO-1234ze.

20. The inhaler of claim 19 wherein said canister is an aerosol canister.

21. The inhaler of claim 19 wherein said medicinal composition is a pressurized medicinal composition.

22. The inhaler of claim 19 wherein said canister comprises a metered dose dispensing valve with a valve stem movable between non-dispensing and dispensing positions.

23. A canister of the type capable of containing the vapor pressure of a propellant contained therein and further containing a medicinal composition suitable for administration to a mammal, said medicinal composition comprising (a) medicinally acceptable propellant and (b) at least one medicinally active compound, said propellant having a toxicity level that is not substantially harmful to the intended recipient of said medicinal compound and comprising at least 50% by weight of HFO-1234, wherein said HFO-1234 consists essentially of transHFO-1234ze.

24. The canister of claim 23 wherein said canister contains an amount of said medicinal composition sufficient to provide a plurality of therapeutically effective doses of said at least one medicinally active compound.

25. The canister of claim 24 wherein said canister contains a medicinal composition for delivering at least one medicinally effective dose of said at least one medicinally active compound to a mammalian body by administration selected from the group consisting of topical, pulmonary, intrapleural, rectal, vaginal, mucosal and combinations of two or more of these.

* * * * *